United States Patent
Shin et al.

(10) Patent No.: US 7,824,323 B2
(45) Date of Patent: Nov. 2, 2010

(54) APPARATUS FOR EVALUATING BLOOD FLOW AND CONTROLLING BLOOD FLOW USING A MAGNETIC FIELD AND METHODS THEREFOR

(75) Inventors: Sang-hoon Shin, Seongnam-si (KR); Ho-seong Gi, Jeollabuk-do (KR); Woo-young Jang, Seoul (KR); Jae-chan Park, Yongin-si (KR); Chan-ho Cho, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 1615 days.

(21) Appl. No.: 11/094,572

(22) Filed: Mar. 31, 2005

(65) Prior Publication Data

US 2005/0222486 A1 Oct. 6, 2005

(30) Foreign Application Priority Data

Mar. 31, 2004 (KR) .................. 10-2004-0022321

(51) Int. Cl.
*A61N 2/00* (2006.01)
(52) U.S. Cl. ........................................... 600/9
(58) Field of Classification Search ............ 600/9–15, 600/504–506, 481
See application file for complete search history.

(56) References Cited

U.S. PATENT DOCUMENTS

| 3,340,867 | A |   | 9/1967 | Kubicek et al. |
|-----------|---|---|--------|---------------|
| 5,176,919 | A |   | 1/1993 | Curri et al. .................. 424/450 |
| 5,856,328 | A |   | 1/1999 | Shinyama et al. ........... 514/253 |
| 5,935,077 | A | * | 8/1999 | Ogle .......................... 600/504 |
| 5,995,857 | A |   | 11/1999 | Toomim et al. ............. 600/322 |
| 6,409,675 | B1 |   | 6/2002 | Turcott ....................... 600/508 |
| 6,589,159 | B2 |   | 7/2003 | Paturu ......................... 600/15 |
| 2004/0044288 | A1 | * | 3/2004 | Gorenberg et al. .......... 600/481 |
| 2004/0116784 | A1 | * | 6/2004 | Gavish ....................... 600/300 |

* cited by examiner

*Primary Examiner*—Charles A Marmor, II
*Assistant Examiner*—Christine D Hopkins
(74) *Attorney, Agent, or Firm*—Cantor Colburn LLP

(57) ABSTRACT

In a blood flow controlling apparatus using a magnetic field for controlling blood flow within a living body, and methods therefor, the blood flow controlling apparatus includes a magnetic field applying unit for supplying the magnetic field and applying the magnetic field to the living body, a blood flow measuring unit for measuring a blood flow signal including information about blood flow, and a blood flow controlling unit for controlling the blood flow according to the measured blood flow signal.

18 Claims, 12 Drawing Sheets

APPARATUS FOR EVALUATING BLOOD FLOW AND CONTROLLING BLOOD FLOW USING A MAGNETIC FIELD AND METHODS THEREFOR

BACKGROUND OF THE INVENTION

1. Field of the Invention

The present invention relates to an apparatus for and a method of controlling blood flow using a magnetic field. More particularly, the present invention relates to an apparatus for and a method of achieving optimally improved blood flow by evaluating a change in blood flow caused by a magnetic field after application of the magnetic field to a living body and providing biofeedback of the results to a user so that the user can control the intensity of the magnetic field and the time the magnetic field is applied.

2. Description of the Related Art

Generally, blood flow can be understood as the flow of blood within a body. Blood flow directly or indirectly affects the health of that body. If there is poor blood flow to the stomach and intestines, a gastroenteric disorder occurs. If blood does not flow properly to the legs, the legs ache, if blood does not flow properly to the knees, arthritis occurs, or if blood does not flow properly to the heart, then heart disease develops. If blood flow to the brain is poor, headaches occur or brain functions decrease. In serious cases, poor blood flow may result in a cerebral infarction, cerebral apoplexy, cerebral hemorrhage, or the like. If blood flow to the lungs is poor, lung diseases occur. In short, if blood flow to any part of the body is not proper, and oxygen and nutrients are not adequately supplied to those parts of the body, waste matters, which results from metabolism, are not removed, and thus pain occurs and diseases develop.

When blood flow difficulties occur in the body, the blood flow can be improved in various ways. For example, blood flow may be improved by warming the body, increasing flexibility of muscles, exercising, taking medications designed to improve blood flow, applying pressure to specific areas of the body using fingers to spread the waste matters to other parts of the body, or directly extracting dead red and white blood cells from different regions of the body.

Recently, active research has been conducted into treating pain and diseases by improving blood flow using a magnetic field. It is well known that such research is greatly effective.

FIG. 1 illustrates a conventional therapeutic device using an electrical connection between a magnetic boot and an electrical source.

One example of such research includes a therapeutic device, as shown in FIG. 1, configured as a magnetic boot 200 to create a magnetic field. The magnetic boot 200 includes an insulated inner layer (not shown), a frame (not shown) formed on the insulated inner layer, wires (not shown) covering the frame, and an outer layer 218. The wires are connected to an electrical source 214 via external cables 215. A magnetic field is the strongest at a tip 220 of the magnetic boot 200. However, the effects of improving blood circulation using the therapeutic device described above are not supported by systematic experiments or data.

In addition, conventional methods of and devices for improving blood circulation usually use medicine or mechanical stimulus, e.g., massage. Particularly, conventional methods for improving blood circulation using new medicine compositions are common. However, there are side effects when blood circulation is improved using pharmaceutical compositions according to the conventional methods. These side effects can cause more serious harm as compared to the benefits obtained by improving the blood circulation of the body.

Other conventional methods include measuring a change in the blood flow of the entire body using impedance and a method of measuring the blood flow of a specific part of the body and providing feedback of the results to a device. However, it is difficult to evaluate the effects of these methods properly.

Still another conventional method includes a method of and apparatus for monitoring a hemodynamic status of a patient by examining blood flow of a specific area of the patient, in which data can be conveyed routinely and automatically. However, such method and apparatus are difficult to use and cannot be applied to all patients.

Therefore, it is difficult to know the actual improvement in blood flow achieved for each person being treated.

SUMMARY OF THE INVENTION

The present invention is therefore directed to an apparatus for and a method of controlling blood flow using a magnetic field, which substantially overcome one or more of the problems due to the limitations and disadvantages of the related art.

It is therefore a feature of an embodiment of the present invention to provide an apparatus for and a method of achieving optimum improvement in blood flow by providing feedback of the change in blood flow caused when a magnetic field is applied to the body of a user to the user so that the user can control the intensity and application time of the magnetic field.

It is therefore another feature of an embodiment of the present invention to provide an apparatus for and a method of evaluating a change in blood flow caused when a magnetic field is applied to a living body.

It is therefore still another feature of an embodiment of the present invention to provide an apparatus and method capable of measuring blood flow, e.g., near a wrist of a living body, and providing feedback of the results to a user, thereby enabling blood flow to be improved more efficiently.

It is therefore yet another feature of an embodiment of the present invention to provide an apparatus and method capable of measuring and controlling blood flow with ease and without harm to the user.

At least one of the above and other features and advantages of the present invention may be realized by providing a blood flow controlling apparatus using a magnetic field for controlling blood flow within a living body, the blood flow controlling apparatus including a magnetic field applying unit for supplying the magnetic field and applying the magnetic field to the living body, a blood flow measuring unit for measuring a blood flow signal including information about blood flow, and a blood flow controlling unit for controlling the blood flow according to the measured blood flow signal.

The blood flow controlling unit may be operable to provide biofeedback of the measured blood flow signal.

The blood flow controlling unit may include a blood flow quantity and blood flow difference calculator for calculating a blood flow quantity and a blood flow difference, a magnetic field intensity calculator for calculating an intensity of the magnetic field applied to the living body, a magnetic field applying time calculator for calculating a time the magnetic field is applied to the living body, and a controller for controlling the magnetic field intensity calculator and the magnetic field applying time calculator using the blood flow quantity and the blood flow difference calculated by the blood flow quantity and blood flow difference calculator.

The blood flow controlling apparatus may further include a mode selecting unit for selecting from a plurality of modes. The mode selecting unit is operable to select one mode from the group including a blood flow improvement evaluation mode, a blood flow quantity monitoring mode, an optimum condition determination mode, and a blood flow improving mode, and wherein the selected mode is input to the controller of the blood flow controlling unit.

The optimum condition determination mode may include an optimum magnetic field applying time determining mode, an optimum magnetic field intensity determining mode, and an optimum magnetic field intensity and applying time determining mode.

The blood flow controlling apparatus may further include an outputting unit.

The outputting unit may display data selected from the group including blood flow quantity, blood flow difference, and optimum magnetic field intensity and applied time, obtained by the blood flow controlling unit, and wherein the outputting unit displays information so that a user may control a blood flow controlling apparatus software including one or more items selected from the group including a start menu, a mode selection menu, and a user history menu.

The outputting unit may be an output device that outputs data obtained by the blood flow controlling unit in a manner selected from print, an audio signal, a two-dimensional visual image, and moving images. The outputting unit may be an output device that displays data obtained from the blood flow controlling unit while measuring the blood flow in real-time to a testee and a tester. The outputting unit may be an output device for analyzing data obtained from the blood flow controlling unit and for additionally outputting medical information or diagnosis.

The magnetic field applying unit may include a monopole stimulus. The magnetic field applying unit may include a first magnet that is a north pole and a second magnet that is a south pole.

The blood flow measuring unit may include a light sensor, wherein the light sensor is either a photoplethysmogram (PPG) or a laser Doppler flowmeter (LDF).

The blood flow measuring unit may be operable to use an electrical impedance method including impedance plethysmography (IPG).

The magnetic field intensity calculator may be operable to receive the blood flow quantity and the blood flow difference calculated by the blood flow quantity and blood flow difference calculator, and continually feedback a magnetic field increased value to the magnetic field applying unit until the blood flow difference reaches a maximum, to find an optimum blood flow quantity, thereby determining an optimum magnetic field.

The magnetic field applying time calculator may be operable to receive the blood flow difference transmitted from the blood flow quantity and blood flow difference calculator and continually feedback a magnetic field applying time increase value to the magnetic field applying unit until the blood flow difference reaches a maximum, to find an optimum blood flow quantity, thereby determining an optimum magnetic field applying time.

The blood flow measuring unit may be operable to measure a radial artery region of a wrist.

At least one of the above and other features and advantages of the present invention may be realized by providing a blood flow evaluating apparatus for examining an effect on blood flow of an apparatus that applies a magnetic field to a predetermined region of a living body, the blood flow evaluating apparatus including a blood flow measuring unit for measuring a blood flow signal including information about blood flow and a blood flow quantity and blood flow difference calculator for calculating a blood flow quantity and a blood flow difference using the blood flow signal measured according to an applied magnetic field, wherein an improvement in blood flow is evaluated using the calculated blood flow quantity and the blood flow difference.

At least one of the above and other features and advantages of the present invention may be realized by providing a blood flow controlling apparatus using a magnetic field, the blood flow controlling apparatus including a magnetic field applying unit for applying the magnetic field to a predetermined region of a living body, a blood flow measuring unit for measuring a blood flow signal including information about blood flow, a mode selecting unit for selecting from among a plurality of modes by a user, a blood flow quantity and blood flow difference calculator for calculating a blood flow quantity and a blood flow difference using the blood flow signal, a controlling unit for generating a control signal according to a mode selected by the mode selecting unit, and a magnetic field controlling unit for controlling the magnetic field using the control signal and the blood flow quantity and difference, and applying the magnetic field to the predetermined region.

The magnetic field controlling unit may include a magnetic field intensity calculator for calculating an intensity of the magnetic field applied to the living body and a magnetic field applying time calculator for calculating a time the magnetic field is applied to the living body.

The magnetic field intensity calculator may be operable to receive the blood flow quantity and the blood flow difference calculated by the blood flow quantity and blood flow difference calculator, and continually feedback a magnetic field increased value to the magnetic field applying unit until the blood flow difference reaches a maximum, to find an optimum blood flow quantity, thereby determining an optimum magnetic field.

The magnetic field applying time calculator may be operable to receive the blood flow difference transmitted from the blood flow quantity and blood flow difference calculator and continually feedback a magnetic field applying time increase value to the magnetic field applying unit until the blood flow difference reaches a maximum, to find an optimum blood flow quantity, thereby determining an optimum magnetic field applying time.

The mode selecting unit may select one mode from the group including mode 0 through mode 4, where mode 0 is for evaluating blood flow improvement, mode 1 is for monitoring the blood flow quantity, mode 2 is determining an optimum magnetic field applying time for improving the blood flow using the magnetic field applying time calculator, mode 3 is for determining an optimum magnetic field intensity for improving the blood flow using the magnetic field intensity calculator, and mode 4 is for controlling an optimum blood flow using the magnetic field applying time calculator and the magnetic field intensity calculator.

At least one of the above and other features and advantages of the present invention may be realized by providing a method of controlling blood flow using a blood flow controlling apparatus that uses a magnetic field, the blood flow controlling apparatus including a magnetic field applying unit for supplying and applying the magnetic field, a mode selecting unit for selecting from among a plurality of modes by a user, a blood flow measuring unit for measuring a blood flow signal that includes information about blood flow, and a blood flow controlling unit for controlling the blood flow according to the measured blood flow signal, the method including selecting a mode by the user and performing an operation selected from the group including evaluating an improvement of blood flow, monitoring a blood flow quantity, determining an optimum condition, and improving blood flow, according to the selected mode.

Evaluating the improvement of blood flow may include setting a magnetic field applying time $T_{end}$ and an intensity of the applied magnetic field B, calculating a blood flow quantity $Q_{i-1}$, applying the magnetic field B for the magnetic field applying time $T_{end}$ and calculating a blood flow quantity $Q_i$, and calculating a difference $(Q_{i-1}-Q_i)$ of the measured blood flow quantities.

The magnetic field applying time $T_{end}$ and the intensity of the applied magnetic field B may be set by the user.

The magnetic field applying time $T_{end}$ may be an optimum magnetic field applying time $T^*$.

Monitoring the blood flow quantity may include calculating blood flow quantity based on the measured blood flow signal, if monitoring the blood flow quantity is selected in the selecting of a mode and selectively ending the process or continually measuring the blood flow, after calculating the blood flow quantity according to the applied magnetic field.

Determining the optimum condition may be a mode for performing feedback of the blood flow signal to determine one of an optimum magnetic field applying time $T^*$ and an optimum magnetic field $B^*$.

The mode for selecting the optimum condition that determines the optimum magnetic field applying time $T^*$ may include setting an intensity B of the applied magnetic field, setting a magnetic field applying time $T_{end}$ and a magnetic field applying time changed value $\Delta T$, calculating a blood flow quantity $Q_{i-1}$ and initializing the magnetic field applying time T, applying the set applied magnetic field B for the magnetic field applying time changed value $\Delta T$ and calculating a blood flow quantity $Q_i$, comparing the magnetic field applying time T to the magnetic field applying time $T_{end}$ and if the magnetic field applying time $T_{end}$ is less, then determining that point of time as the optimum magnetic field applying time $T^*$ and terminating the process, and comparing the blood flow quantity $Q_i$ to the blood flow quantity $Q_{i-1}$ and if $Q_i \geq Q_{i-1}$, then determining the optimum magnetic field applying time $T^*$ as the magnetic field applying time T, if $Q_i < Q_{i-1}$, then setting the value of $Q_{i-1}$ to be $Q_i$, adding the magnetic field applying time changed value $\Delta T$ to the magnetic field applying time T and returning to the application of the magnetic field and the calculation of the blood flow quantity $Q_i$.

The intensity of the applied magnetic field may be set, or set to another constant time, by the user and the optimum magnetic field applying time may be obtained by varying only the magnetic field applying time.

The mode for selecting the optimum condition that determines the optimum magnetic field $B^*$ may include after setting a magnetic field applying time $T_c$, an applied magnetic field initial value $B_{start}$, a maximum applied magnetic field intensity $B_{end}$, and an intensity B of the applied magnetic field, calculating blood flow quantity $Q_{i-1}$ by having the applied magnetic field initial value $B_{start}$ as the intensity B of the applied magnetic field, applying the applied magnetic field with intensity B for the magnetic field applying time $T_c$ and calculating blood flow quantity $Q_i$, if $Q_i < Q_{i-1}$, determining the optimum magnetic field $B^*$ as the intensity B of the applied magnetic field, if $Q_i \geq Q_{i-1}$, setting the value of $Q_{i-1}$ to be $Q_i$, increasing the applied magnetic field B by an applied magnetic field changed value $\Delta B$ and returning to the application of the magnetic field and the calculation of the blood flow quantity $Q_i$.

The mode for selecting the optimum condition that determines the optimum magnetic field $B^*$ may have the magnetic field applying time set to the optimum magnetic field applying time $T^*$, or to another constant time set by the user, and the optimum magnetic field intensity may be obtained by varying the intensity of the magnetic field.

The mode for improving the blood flow may perform an optimum blood flow improvement using the optimum magnetic field applying time $T^*$ and the optimum magnetic field $B^*$ obtained by the mode for determining the optimum condition.

The mode for improving the blood flow may include setting the optimum magnetic field applying time $T^*$ and the optimum magnetic field $B^*$, calculating a blood flow quantity $Q_{i-1}$, calculating a blood flow quantity $Q_i$ by applying the optimum magnetic field $B^*$ for the optimum magnetic field applying time $T^*$, and calculating and storing a blood flow difference $\Delta Q = Q_i - Q_{i-1}$ and terminating the process.

At least one of the above and other features and advantages of the present invention may be realized by providing a method of controlling blood flow using a magnetic field within a living body, the method including applying the magnetic field to a predetermined region, measuring a blood flow signal including information about blood flow, and controlling the blood flow according to the measured blood flow signal.

Controlling the blood flow may include calculating a blood flow quantity and a blood flow difference, calculating an intensity of the applied magnetic field, calculating a time the magnetic field is applied, and controlling the calculated intensity of the applied magnetic field and the time the magnetic field is applied using the calculated blood flow quantity and the blood flow difference.

Calculating the intensity of the applied magnetic field may include calculating an optimum magnetic field intensity $B^*$ by continually providing feedback of an increased value of the intensity of the magnetic field to a magnetic field applying unit until the blood flow difference calculated during the calculation of the blood flow quantity and the blood flow difference reaches a maximum to determine an optimum blood flow quality.

Calculating the time the magnetic field is applied may include calculating an optimum magnetic field applying time by continually providing feedback of an increased value of the magnetic field applying time to a magnetic field applying unit until the blood flow difference calculated during the calculation of the blood flow quantity and the blood flow difference, reaches a maximum to determine an optimum blood flow quality.

Calculating the blood flow quantity and the blood flow difference may include measuring in a radial artery region of a wrist, which has distinctive characteristics of an artery.

BRIEF DESCRIPTION OF THE DRAWINGS

The above and other features and advantages of the present invention will become more apparent to those of ordinary skill in the art by describing in detail exemplary embodiments thereof with reference to the attached drawings in which.

DETAILED DESCRIPTION OF THE INVENTION

Figure 1:
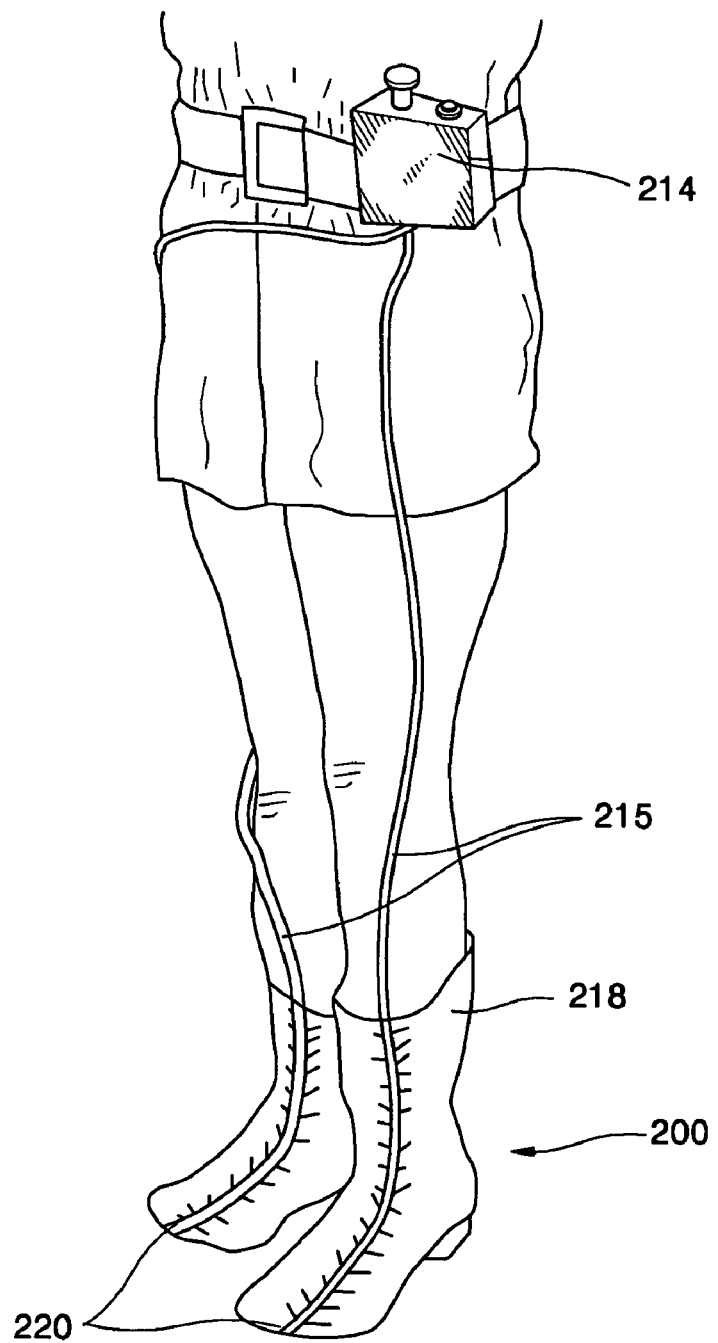
FIG. 1 illustrates a conventional therapeutic device using an electrical connection between a magnetic boot and an electrical source.

Korean Patent Application No. 10-2004-0022321, filed on Mar. 31, 2004, in the Korean Intellectual Property Office, and entitled: "Apparatus for Controlling Blood Flow Using a Magnetic Field and Methods Therefor," is incorporated by reference herein in its entirety.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Figure 2:
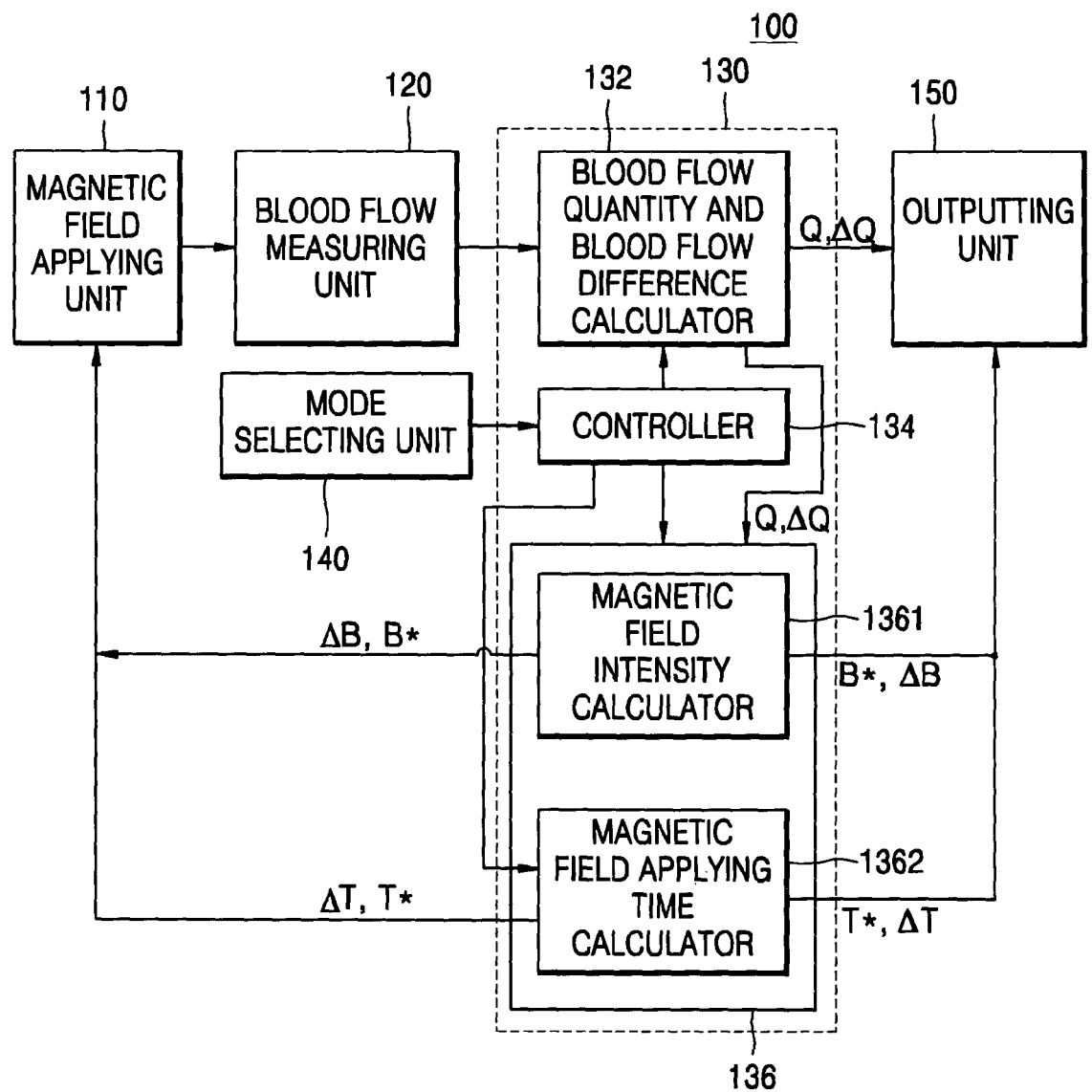
FIG. 2 is a block diagram of a blood flow controlling apparatus using a magnetic field according to an exemplary embodiment of the present invention.

FIG. 2 is a block diagram of a blood flow controlling apparatus 100 using a magnetic field according to an exemplary embodiment of the present invention. Referring to FIG. 2, the blood flow controlling apparatus 100 includes a magnetic field applying unit 110, a blood flow measuring unit 120, a blood flow controlling unit 130 having a blood flow quantity and blood flow difference calculator 132, a controller 134, and a magnetic field controller 136, a mode selecting unit 140, and an outputting unit 150. According to the present exemplary embodiment of the present invention, the magnetic field controller 136 includes a magnetic field intensity calculator 1361 and a magnetic field applying time calculator 1362. In addition, the blood flow quantity and blood flow difference calculator 132 may include a blood flow quantity calculator (not shown) and a blood flow difference calculator (not shown).

In another exemplary embodiment, the blood flow quantity and blood flow difference calculator 132 and the controller 134 may be additionally incorporated into the magnetic field controller 136 of the blood flow controlling unit 130.

In the blood flow controlling apparatus 100, the magnetic field applying unit 110 may include a permanent magnet or an electromagnet. Further, the magnetic field applying unit 110 may be formed to contact or to avoid contact with a predetermined area of the living body and may be configured to apply a monopole or a directional pole to the area where the magnetic field is to be applied.

The monopole may be configured so that a north pole can be placed on a predetermined area. The directional pole, in which two magnets form a pair, may be configured so that a magnetic field has north/south polarities parallel to a contacting surface by adhering the north pole of one magnet, to the south pole of the other adjacent magnet, on a predetermined area. Furthermore, when applying the directional magnet to a predetermined area, the direction of the magnetic field may preferably coincide with the directions in which the blood flows through arteries and veins. Therefore, the improvement of blood flow can be maximized.

After the magnetic field is applied to a living body by the magnetic field applying unit 110, the blood flow measuring unit 120 measures a blood flow signal in a blood flow measuring region, which is a predetermined region of the body. The blood flow measuring region may coincide with the area where the magnetic field is applied to, may be an area adjacent to that area, or may be another area. The measuring region may preferably be a radial artery region of the wrist.

In addition, in the present exemplary embodiment, a blood flow quantity was detected using the blood measuring unit 120 configured in an optical sensor including, e.g., an ultrasound sensor, a photoplethysmogram (PPG), or a laser Doppler flowmeter (LDF), and an electrical impedance method including, e.g., an impedance plethysmography (IPG) method.

Figure 3:
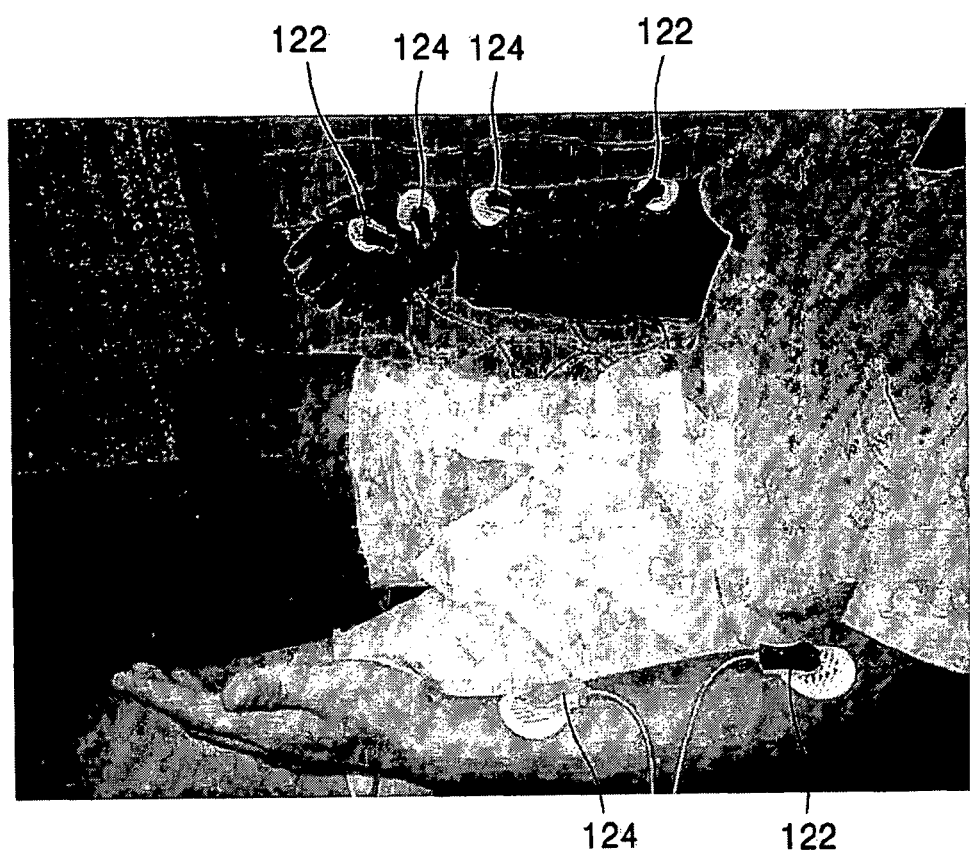
FIG. 3 is a view to explain how to measure a blood flow quantity near a radial artery region of a human wrist using an impedance plethysmography (IPG) method according to an exemplary embodiment of the present invention.

FIG. 3 is a view to explain how to measure a blood flow quantity near the radial artery region of the wrist using IPG. In the present exemplary embodiment, magnets were removed after application of the magnetic field to a predetermined region of the body, and a pair of first poles 122 was adhered to the palm and a top portion of the forearm and current was applied to the first poles 122. Next, a pair of second poles 124 was adhered between the first poles 122 and the difference of the impedance value was observed by measuring the impedance value. Thus, the difference in the blood flow quantity can be measured using the impedance value measured. In addition, in the present exemplary embodiment, in order to obtain a more accurate blood flow quantity measurement value, data of both arms were compared.

Figure 4A:
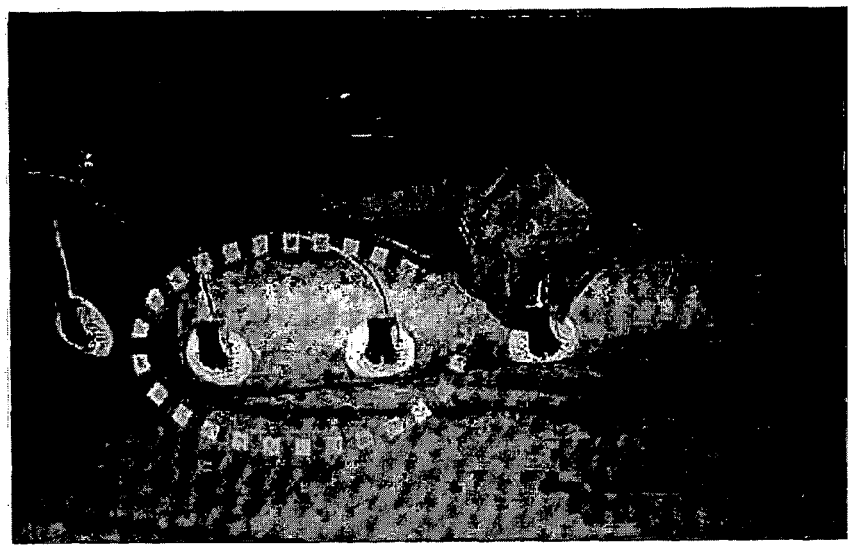
FIGS. 4A through 4C are views to explain how to measure the effects of a magnetic field on different parts of a living body according to exemplary embodiments of the present invention.
Figure 4B:
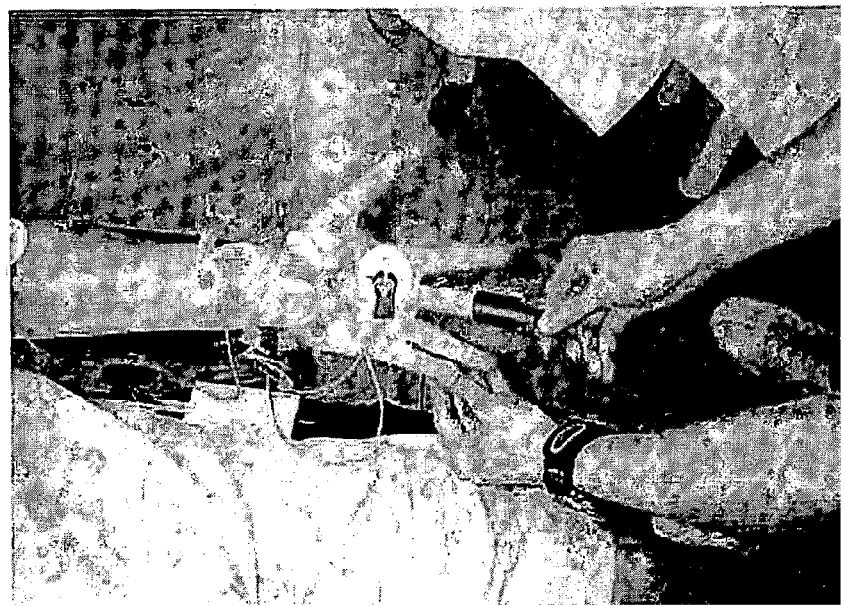
Figure 4C:

FIGS. 4A through 4C are views to explain how to measure effects of a magnetic field on different parts of the body according to exemplary embodiments of the present invention. FIG. 4A is a photograph of measuring a change in the blood flow quantity when a magnetic field is applied to a leg of a testee. FIG. 4B is a photograph of measuring a change in the blood flow quantity when a magnetic field is applied to a wrist of the testee.

The results of the present exemplary embodiment show that it is more significant to measure the change in the blood flow in the radial artery region of the wrist rather than in the leg region. The results of the experiment is shown in Table 1 below:

TABLE 1

| Blood Flow Quantity | Leg (n = 30) | Wrist (n = 50) |
|---|---|---|
| Left | 0.851 | 0.001 |
| Right | 0.474 | 0.001 |

In Table 1, a paired T-test method was used to compare the results of the blood flow quantity of the leg region and the wrist region of a male adult in his twenties.

FIG. 4C is a photograph showing an experiment in which the results of the blood flow quantity in the wrist area when a real magnet and a fake magnet were used on fifty male adults in their twenties are compared using the paired T-test method, to examine the effects of the magnetic field on the body. The results of the experiment are shown in Tables 2 and 3 below. Table 2 shows the results when the fake and real magnets are used on the left wrist. Table 3 shows the results when the fake and real magnets are used on the right wrist.

TABLE 2

|  | Mean | Std. Dev. | SE Mean |
| --- | --- | --- | --- |
| Fake Magnet (Left) | 2.36 | 7.85 | 1.11 |
| Real Magnet (Left) | −2.38 | 7.77 | 1.10 |
| Difference | 4.74 | 9.26 | 1.31 |

The results shown in Table 2 show a 95% reliability section for the mean difference of (2.11, 7.37), and the paired T-test method has the mean difference of zero, wherein the mean difference has a T-value of 3.62 and a P-value of 0.001.

TABLE 3

|  | Mean | Std. Dev. | SE Mean |
| --- | --- | --- | --- |
| Fake Magnet (Right) | 2.78 | 8.21 | 1.16 |
| Real Magnet (Right) | −2.86 | 7.67 | 1.08 |
| Difference | 5.64 | 11.64 | 1.65 |

The results shown in Table 3 show a 95% reliability section for the mean difference of (2.34, 8.95), and the paired T-test method has the mean difference of zero, wherein the mean difference has a T-value of 3.43 and a P-value of 0.001.

According to the present exemplary embodiment, the blood flow signal detected at the blood flow measuring unit 120 is input to the blood flow quantity and blood flow difference calculator 132 within the blood flow controlling unit 130.

Referring back to FIG. 2, the mode selecting unit 140 is configured to be able to select from among a plurality of modes. In the present exemplary embodiment, it is set to have five (5) modes, viz., mode 0, mode 1, mode 2, mode 3 and mode 4. Detailed descriptions of the five modes are as follows:

Mode 0 is a mode to evaluate the effect of the magnetic field applying unit 110. This mode outputs a difference in blood flow quantity before and after application of the magnetic field and evaluates a degree of change in the blood flow with respect to the applied magnetic field. Particularly, mode 0 is useful in evaluating an effect of therapeutic devices using a magnetic field, such as a magnetic bracelet or a magnetic mat. Mode 1 is a mode to output the current blood flow quantity without controlling an intensity of the magnetic field or a time the magnetic field is applied, and to monitor the results. Mode 2 is a mode to determine an optimum magnetic field applying time by controlling only the application time of the magnetic field when the magnetic field is constant. Mode 3 is a mode to determine an optimum magnetic field intensity by controlling only the intensity of the magnetic field when the application time of the magnetic field is constant. Mode 4 is a mode to actually improve the blood flow using the optimum magnetic field applying time and magnetic field intensity obtained in modes 2 and 3.

According to the present exemplary embodiment, a user may select one of the five modes according to the user's needs and input it to the mode selecting unit 140. Then, the mode selecting unit 140 transmits the selection signal to the controller 134 within the blood flow controlling unit 130.

The blood flow controlling unit 130 may directly output the blood flow signal measured at the blood flow measuring unit 120 to the outputting unit 150, or the user may control the characteristics of the magnetic field applied to the blood flow controlling apparatus 100 to optimize the improvement of the blood flow based on the blood flow signal.

The blood flow quantity and blood flow difference calculator 132 calculates the blood flow quantity using the blood flow signal obtained from the blood flow measuring unit 120. Also, the blood flow quantity and blood flow difference calculator 132 transmits the blood flow quantity Q and/or blood flow difference $\Delta Q$ calculated based on the blood flow signal obtained from the blood flow measuring unit 120 to the outputting unit 150 and/or the magnetic field controller 136. Although not illustrated in FIG. 2, the blood flow quantity and blood flow difference calculator 132 may include a blood flow difference calculator that calculates the blood flow difference $\Delta Q$ separately.

In addition, the controller 134 controls the blood flow quantity and blood flow difference calculator 132 and the magnetic field controller 136 depending on the mode selected by the user using the mode selecting unit 140. For example, if mode 3 is selected, the controller 134 transmits the blood flow quantity Q and blood flow difference $\Delta Q$ calculated at the blood flow quantity and blood flow difference calculator 132 to the magnetic field intensity calculator 1361. In this mode, the magnetic field intensity calculator 1361 continually feedbacks a magnetic field increased value $\Delta B$ to the magnetic field applying unit 110 until the blood flow difference $\Delta Q$ received from the blood flow quantity and blood flow difference calculator 132 is maximized, so that the magnetic field intensity calculator 1361 calculates the optimum blood flow quantity Q and transmits the optimum magnetic field B* to the outputting unit 150.

Figure 5A:
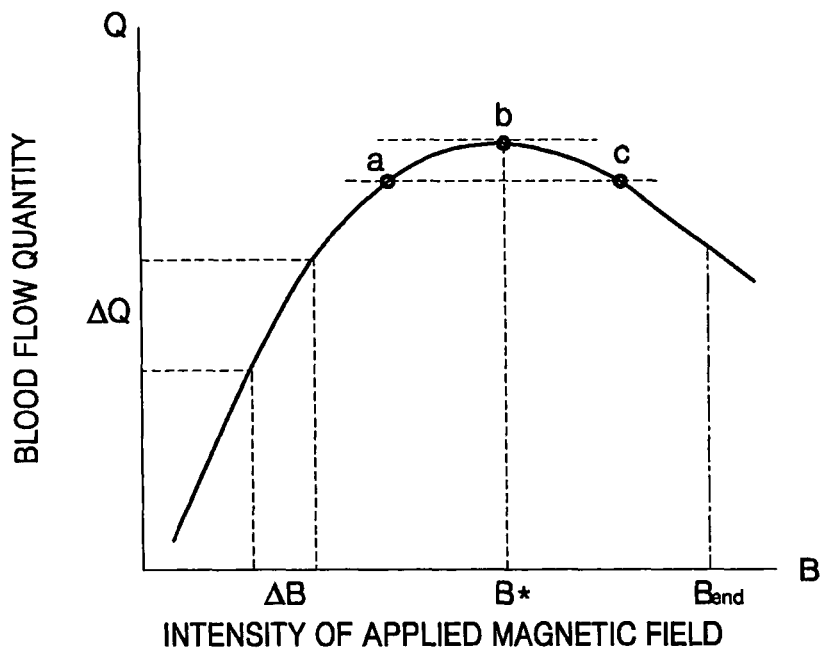
FIG. 5A is a graph showing a change in blood flow as an intensity of an applied magnetic field is altered according to an exemplary embodiment of the present invention.

FIG. 5A is a graph showing change in blood flow as intensity of the applied magnetic field is altered according to an exemplary embodiment of the present invention. Referring to FIG. 5A, an x-axis represents a magnetic field B and a y-axis represents a blood flow quantity Q. In addition, $\Delta B$ is an increased value of the applied magnetic field. If the change of the blood flow quantity Q is measured after the intensity of the applied magnetic field is increased by $\Delta B$, a blood flow difference $\Delta Q$ is measured. $B_{end}$ on the graph is the maximum limit of the applied magnetic field. B* is the intensity of the magnetic field that corresponds to an inflection point b, which indicates the maximum blood flow quantity.

Once again referring to FIG. 2, when mode 2 is selected, the controller 134 commands the blood flow quantity and blood flow difference calculator 132 to transmit the blood flow quantity Q and the blood flow difference $\Delta Q$ to the magnetic field applying time calculator 1362 of the magnetic field controller 136. In this mode, the magnetic field applying time calculator 1362 continually feedbacks a magnetic field applying time changed value $\Delta T$ to the magnetic field applying unit 110 until the blood flow difference $\Delta Q$ reaches a maximum to find the optimum blood flow quantity Q, and transmits an optimum magnetic field applying time T* to the outputting unit 150.

Figure 5B:
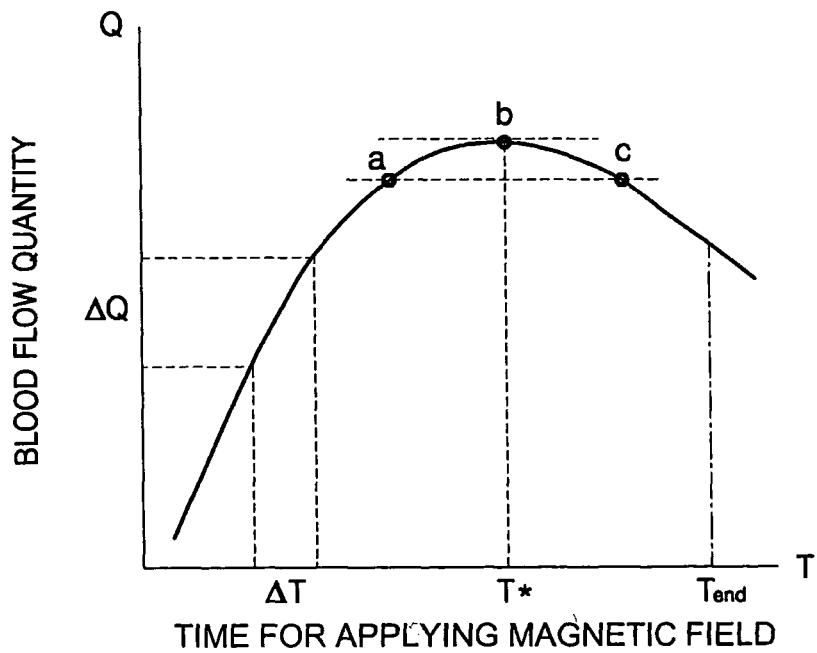
FIG. 5B is a graph showing a change in blood flow as a magnetic field applying time is altered according to an exemplary embodiment of the present invention.

FIG. 5B is a graph showing change in blood flow quantity as the magnetic field applying time is altered according to an exemplary embodiment of the present invention. Referring to FIG. 5B, an x-axis represents time T and a y-axis represents a blood flow quantity Q. In addition, ΔT is the magnetic field applying time changed value. If the change of the blood flow quantity Q is measured after the magnetic field applying time is increased by ΔT, a blood flow difference ΔQ is measured. $T_{end}$ on the graph is the maximum limit of the magnetic field applying time. T* is the magnetic field applying time that corresponds to an inflection point b, which indicates the maximum blood flow quantity.

The magnetic field intensity calculator 1361 increments the intensity of the magnetic field until $B_{end}$ when the magnetic field applying time is fixed or the optimum magnetic field applying time is found, to find the blood flow quantity Q having maximum blood flow difference ΔQ.

Similarly, the magnetic field applying time calculator 1362 increments the magnetic field applying time until $T_{end}$ when the intensity of the magnetic field is fixed or the optimum intensity of the magnetic field is found, to find the magnetic field applying time T* having maximum blood flow difference ΔQ.

When mode 0 is selected, the controller 134 controls the blood flow difference calculator 132 that evaluates the effect of the magnetic field on the blood flow quantity based on the measured value of the blood flow signal by the blood flow measuring unit 120, depending on whether the magnetic field is applied by the magnetic field applying unit 110. More specifically, the controller 134 controls the blood flow difference calculator 132 to evaluate the blood flow quantity when the magnetic field is applied by the magnetic field applying unit 110.

When mode 1 is selected, the controller 134 controls the monitoring of the value of the blood flow signal measured by the blood flow measuring unit 120 according to the applied magnetic field by the magnetic field applying unit 110.

The mode selecting unit 140 may be configured as a manual device. Alternatively, the blood flow control apparatus 100 may be configured to automatically perform the control operations in each mode and selection of each mode.

The outputting unit 150 displays data, e.g., the blood flow quantity Q, the blood flow difference ΔQ, the optimum magnetic field intensity B*, and the optimum magnetic field applying time T*, received from the blood flow controlling unit 130. If needed, it is possible to configure the outputting unit 150 to additionally display data such as the selected mode, the magnetic field intensity changed value ΔB, and the magnetic field applying time changed value ΔT.

The outputting unit 150 may be an output device that outputs the above-described data to the user in print form, audio signals, a two-dimensional visual image, or moving images.

Also, the outputting unit 150 may be an output device that displays the above-described data while they are being measured so that the testee and a tester may see the results in real-time.

In addition, the outputting unit 150 may be an output device that not only displays the above-described data, but also includes blood flow controlling device software having a start menu, a mode selection menu, a user history menu, and the like, which the user can use. Further, the results may be analyzed and output together with general medical information or diagnosis.

As another alternative, the outputting unit 150 may be an output device that outputs the above-described data together with special sounds to alert the user.

Figure 6:
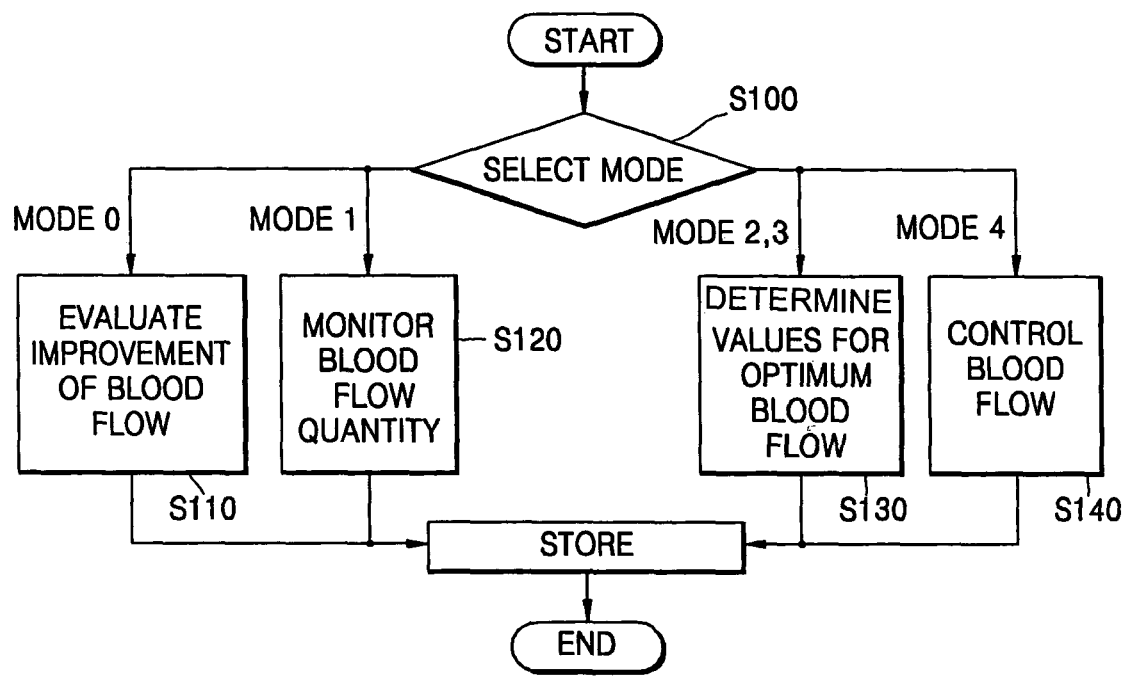
FIG. 6 is a flow chart of a method of controlling blood flow using a magnetic field according to an exemplary embodiment of the present invention.

FIG. 6 is a flow chart of a method of controlling blood flow using a magnetic field according to an exemplary embodiment of the present invention. In the method, first, in Operation S100, a user selects a mode according to the purpose of using the blood flow control apparatus 100. When mode 0 is selected, in Operation S110, the degree of blood flow improvement according to an application of the magnetic field is evaluated. When mode 1 is selected, in Operation S120, an operation of monitoring the blood flow quantity is performed. When modes 2 or 3 are selected, in Operation S130, an operation of determining an optimum intensity of the applied magnetic field or an optimum magnetic field applying time is performed. When mode 4 is selected, in Operation S140, an operation of controlling blood flow to achieve optimum blood flow improvement is performed.

When measuring the blood flow at a predetermined region of the living body after application of the magnetic field according to the present exemplary embodiment, the blood flow measuring region may coincide with the area to which the magnetic field is applied, may be an adjacent area to where the magnetic field is applied, or may be another area. The blood flow measuring region is preferably the radial artery region of the wrist, which is a region with distinctive characteristic of the radial artery.

Subsequently, the results of Operations S100 through S140 are stored or output. The outputting operation displays the above-described exemplary data, e.g., the blood flow quantity Q, the blood flow difference ΔQ, the optimum magnetic field intensity B*, and the optimum magnetic field applying time T*, received from the blood flow controlling unit 130, and may also display the selected mode, magnetic field intensity changed value ΔB, and magnetic field applying time changed value ΔT.

The operations performed in each mode will now be explained in more detail.

Figure 7A:
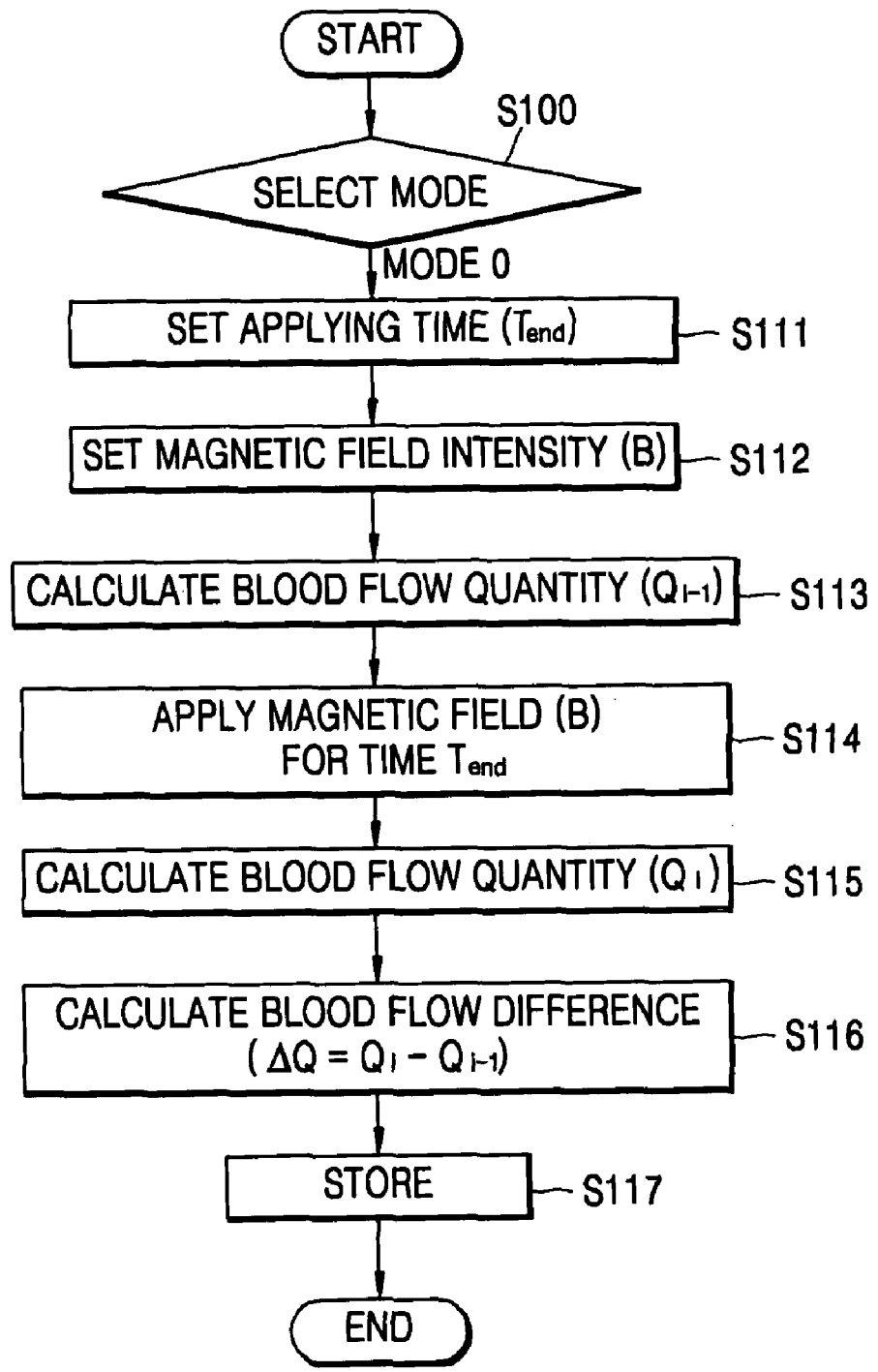
FIG. 7A is a flow chart of an operation of evaluating blood flow improvement in the method shown in FIG. 6.

FIG. 7A is a flow chart explaining the operation of evaluating the blood flow improvement, i.e., Operation S110 of FIG. 6. First, in Operation S100, the user selects an appropriate mode. Operation S110 is performed when the user selects mode 0.

When mode 0 is selected in Operation S100, in Operation S111, a maximum magnetic field applying time, i.e., the maximum limit $T_{end}$ of the magnetic field applying time, is set. A value determined by experience may be used as the maximum limit $T_{end}$. According to the present exemplary embodiment, $T_{end}$ is the time that corresponds to $T_{end}$ of FIG. 5. In Operation S112, the magnetic field intensity B is set.

In Operation S113, blood flow quantity $Q_{i-1}$ is calculated at a predetermined region of the living body, e.g., radial artery region, when no separate external magnetic field is applied. Then, in Operation S114, a magnetic field B is applied to a predetermined region of the living body for a predetermined time $T_{end}$. After the magnetic field B has been applied for the predetermined time $T_{end}$, in Operation S115, blood flow quantity $Q_i$ is calculated.

Then, in order to determine a change in blood flow quantity, in Operation S116, a blood flow difference ($\Delta Q = Q_i - Q_{i-1}$) is calculated. In Operation S117, the blood flow difference ΔQ is stored. According to the present exemplary embodiment, the blood flow controlling apparatus 100 may include a daily checkup function by incorporating history functions that enable the user to use the stored data as comparison data if the user reuses the stored data, by displaying an average stability value for each user since the stored data has an accumulated mean value as the number of times the blood flow controlling apparatus 100 is used increases, or by incorporating tendency graph characteristic data for the number of times the user uses blood flow controlling apparatus 100.

While $T_{end}$ may be a value set by the user, in the following description, it is preferable that $T_{end}$ is an optimum magnetic field applying time T*, which will be calculated in the following operations.

Figure 7B:
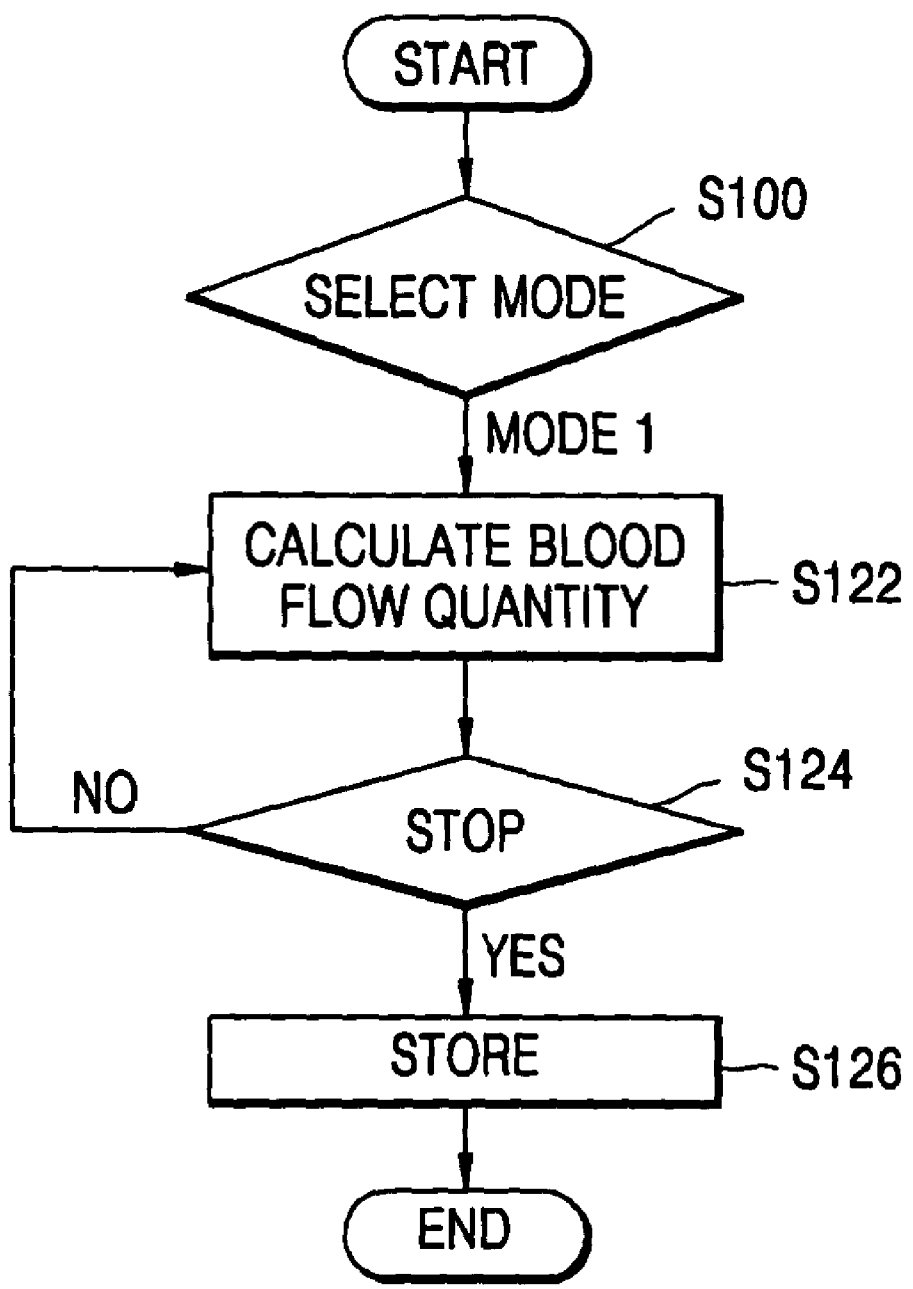
FIG. 7B is a flow chart of an operation of monitoring blood flow quantity in the method shown in FIG. 6.

FIG. 7B is a flow chart explaining the operation of monitoring blood quantity, i.e., Operation S120 of FIG. 6.

When mode 1 is selected in Operation S100, in Operation S122, the blood flow quantity Q is calculated. Then, in Operation S124, when the user no longer wants to monitor the blood flow quantity Q as the magnetic field is applied in real-time, the user presses a stop button. When the stop button is pressed, in Operation S126, the data is stored and the operation is terminated.

If the user does not press the stop button in Operation S124, the blood flow quantity Q is measured continually, and accordingly performs the operation of calculating the blood flow, i.e., Operation S122, and monitors the blood flow quantity Q in real-time.

Figure 7C:
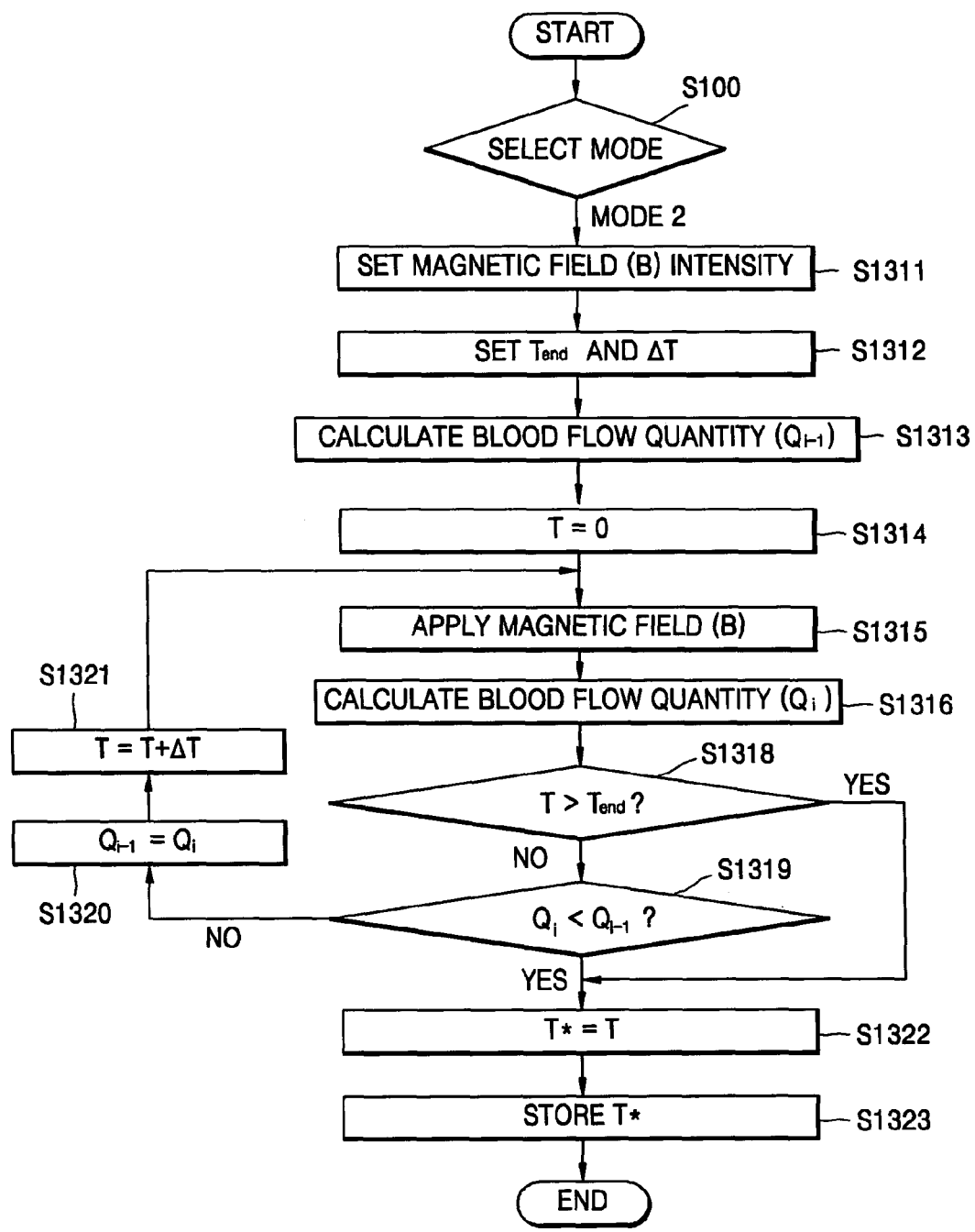
FIG. 7C is a flow chart of an operation of determining an optimum blood flow when mode 2 is selected in the method shown in FIG. 6.

FIG. 7C is a flow chart explaining the operation of determining the optimum blood flow, i.e., Operation S130, when mode 2 is selected in the method of FIG. 6. First, in Operation S100, the user selects a mode appropriate for the desired usage of the user, and the following description relates to the selection of mode 2. Mode 2 is a mode in which the intensity of the magnetic field is adjusted to the optimum magnetic field intensity, or to another value set by the user, and the time the magnetic field is applied is varied to determine the optimum magnetic field applying time.

When mode 2 is selected in Operation S100, in Operation S1311, a predetermined magnetic field intensity B is set by the user. After the maximum magnetic field applying time $T_{end}$ and the magnetic field applying time changed value ΔT are set in Operation S1312, in Operation S1313, a blood flow quantity $Q_{i-1}$ is calculated.

In Operation S1314, the magnetic field applying time T is initialized to zero (0), and, in Operation S1315, the predetermined magnetic field B is applied. In Operation S1316, a blood flow quantity $Q_i$ is calculated. After the blood flow quantity $Q_i$ is calculated, in Operation S1318, it is determined whether the magnetic field applying time T is greater than the maximum magnetic field applying time $T_{end}$. If the magnetic field applying time T is greater than the maximum magnetic field applying time $T_{end}$, in Operation S1322, the optimum magnetic field applying time T* is set as the magnetic field applying time T. If the magnetic field applying time T is not greater than the maximum magnetic field applying time $T_{end}$, in Operation S1319, then the blood flow quantities $Q_i$ and $Q_{i-1}$ are compared, and if the blood flow quantity Q1 is less, the magnetic field applying time T at that moment is set and stored as the optimum magnetic field applying time T* in Operations S1322 and S1323, respectively, and the operation is terminated.

If the blood flow quantity $Q_i$ is not less than the blood flow quantity $Q_{i-1}$, in Operation S1320, $Q_{i-1}$ is set to $Q_i$. Then, in Operation S1321, the magnetic field applying time changed value ΔT is added to T and the process returns back to Operation S1315 to repeat the application of the magnetic field B for the magnetic field applying time changed value ΔT and the calculation of the blood flow quantity $Q_i$.

The optimum magnetic field applying time T* stored in Operation S1323 may be used as an optimum magnetic field applying time in mode 4.

Figure 7D:
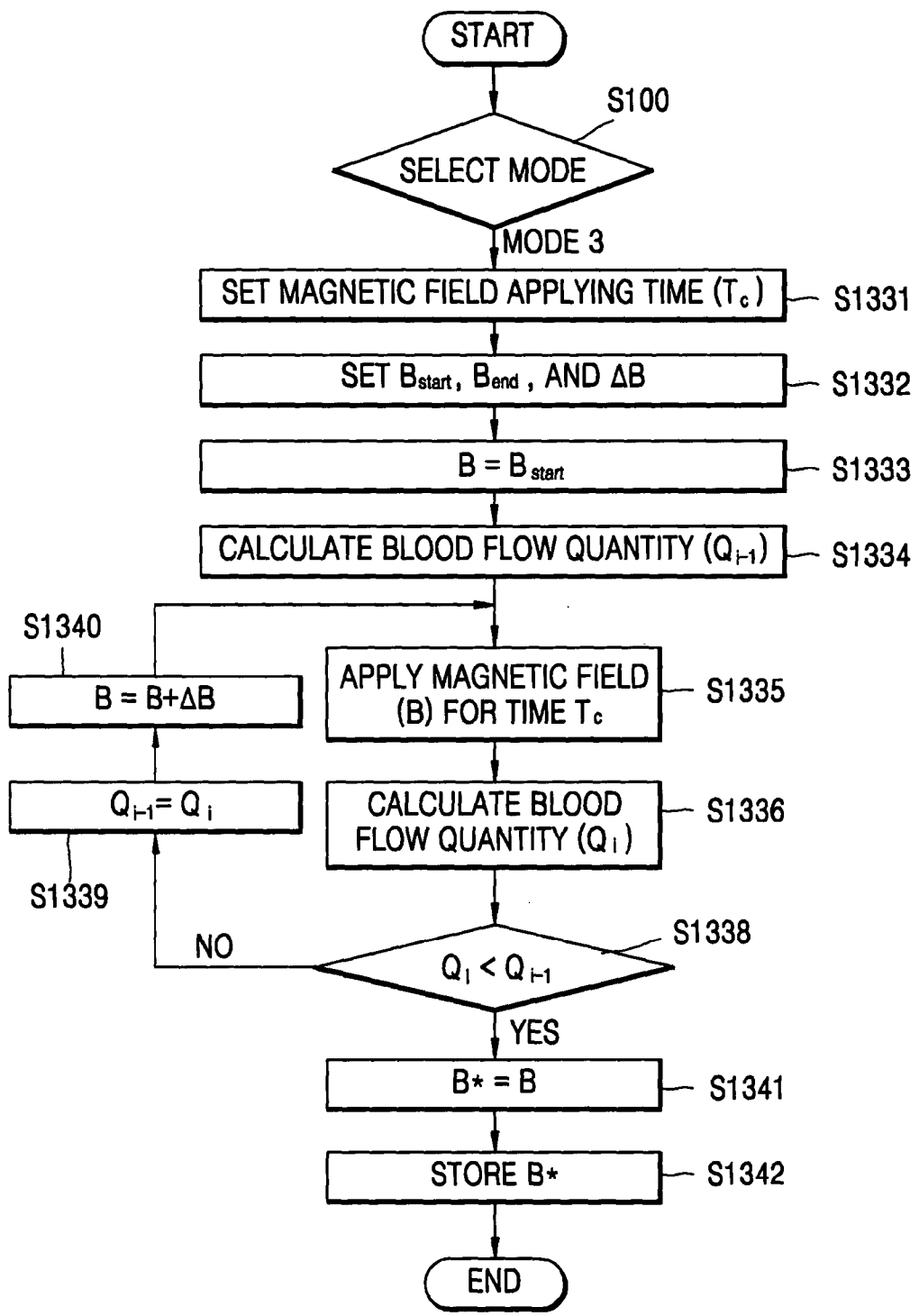
FIG. 7D is a flow chart of an operation of determining an optimum blood flow when mode 3 is selected in the method shown in FIG. 6.

FIG. 7D is a flow chart explaining the operation of determining the optimum blood flow, i.e., Operation S130, when mode 3 is selected in the method of FIG. 6. First, in Operation S100, the user selects an appropriate mode. In the following description, mode 3 is selected. Mode 3 is a mode wherein the application time of the magnetic field is set to the optimum magnetic field applying time T*, or to another value set by the user, and the intensity of the magnetic field is varied to determine a value of an optimum applied magnetic field B*.

After mode 3 is selected in Operation S100, in Operation S1331, a predetermined magnetic field applying time $T_c$ that the user may determine is set. In Operation S1332, an intensity $B_{start}$ of a first applying magnetic field, an intensity $B_{end}$ of the maximum magnetic field to be measured, and a magnetic field increased value ΔB are set. In Operation S1333, the magnetic intensity B is set as $B_{start}$.

Then, in Operation S1334, while no magnetic field is applied, a blood flow quantity $Q_{i-1}$ is calculated. In Operation S1335, the magnetic field B is applied for the predetermined magnetic field applying time $T_c$, and then, in Operation S1336, a blood flow quantity $Q_i$ after application of the magnetic field B is applied for the predetermined magnetic field applying time $T_c$ is calculated.

In Operation S1338, the blood flow quantities $Q_i$ and $Q_{i-1}$ are compared. If $Q_i$ is not less than $Q_{i-1}$, $Q_i$ is stored as the value of $Q_{i-1}$ in Operation S1339, and the applied magnetic field B is increased by the magnetic field increased value ΔB in Operation S1340, and the process goes back to Operation S1335 to apply the magnetic field. If Q1 is less than $Q_{i-1}$, an optimum applied magnetic field intensity B* is set as B in Operation S1341, and the value of B* is stored in Operation S1342. Here, the optimum applied magnetic field intensity B* may be used in mode 4.

Figure 7E:
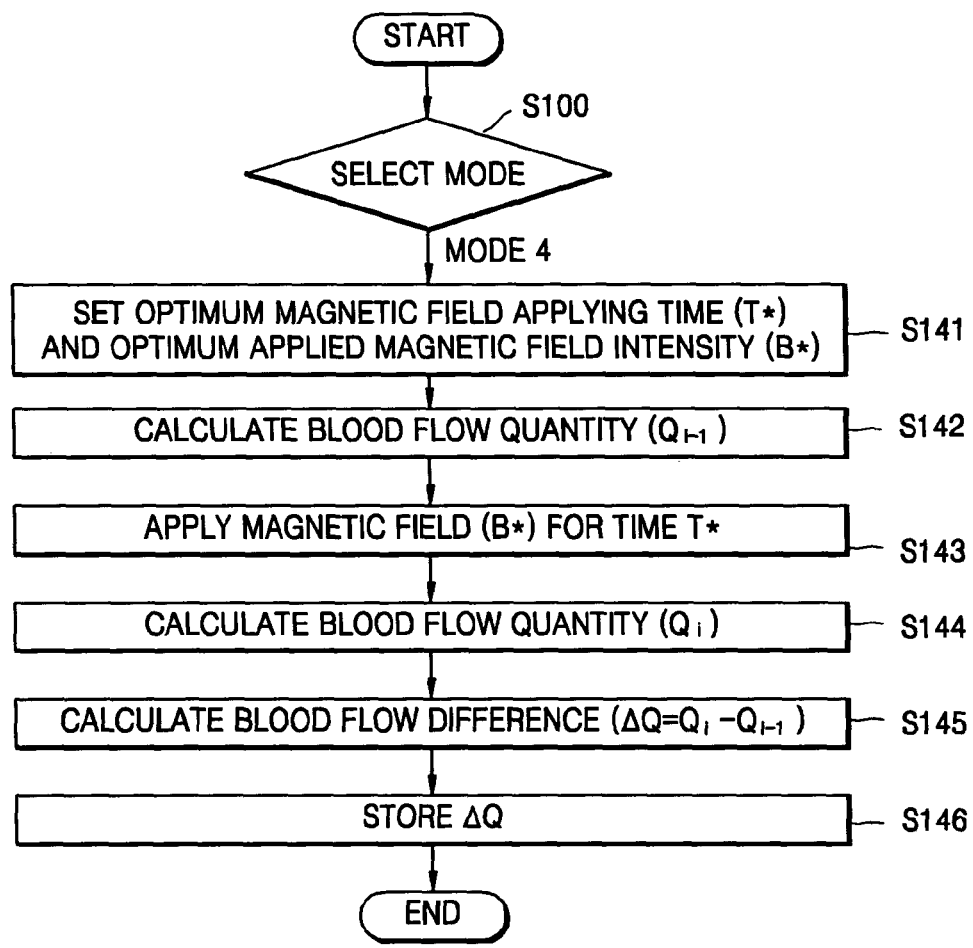
FIG. 7E is a flow chart of an operation of controlling blood flow when mode 4 is selected in the method shown in FIG. 6.

FIG. 7E is a flow chart explaining the operation of controlling the blood flow, i.e., Operation S140, when mode 4 is selected in the method of FIG. 6. First, in Operation S100, the user selects an appropriate mode. In this case, the user selects mode 4. Mode 4 is a mode in which the blood flow is improved using the optimum magnetic field applying time T* and the optimum applied magnetic field intensity B* determined in modes 2 and 3.

When mode 4 is selected in Operation S100, in Operation S141, the optimum magnetic field applying time T* and the optimum applied magnetic field intensity B* are set. The optimum magnetic field applying time T* and the optimum applied magnetic field intensity B* may be the values obtained in modes 2 and 3.

In Operation S142, a blood flow quantity $Q_{i-1}$ from a predetermined region of the living body, e.g., radial artery region, is calculated. The blood flow quantity $Q_{i-1}$ is measured when no magnetic field is applied.

Next, in Operation S143, the optimum applied magnetic field intensity B* is applied for the optimum magnetic field applying time T*. In Operation S144, a blood flow quantity $Q_i$ is calculated. The blood flow quantity $Q_i$ is the blood flow quantity when the optimum applied magnetic field intensity B* is applied for the optimum magnetic field applying time T* set in modes 2 and 3. In Operation S145, a blood flow difference $\Delta Q = Q_i - Q_{i-1}$ is calculated. Subsequently, in Operation S146, the blood flow difference ΔQ is stored and the operation is terminated.

The reason for storing the data in each mode is to allow analysis of the result in view of previous measurements since the optimum magnetic field applying time and the optimum magnetic field intensity may change due to the daily conditions of the user, or under the circumstances and environment in which the measurements were taken.

In addition, although the above-described blood flow controlling apparatus 100 was configured to have an exemplary five (5) modes in the present exemplary embodiment, other configurations are possible. For example, an additional mode may include determining an optimum condition by comparing the result obtained when magnetic field is applied using a permanent magnet and an electromagnet. Further, another mode may include determining an optimum condition by comparing the result obtained when the blood flow controlling apparatus 100 is operated by hand or automatically. The blood flow controlling apparatus 100 may be configured by combining such various modes.

Detailed characteristics of the blood flow controlling apparatus 100 according to exemplary embodiments of the present invention are identified below. The blood flow controlling apparatus 100 may be used by combining one or more of the following items.

First, a blood flow quantity in a certain area of a living body may be measured when no magnet is used. Second, an effect of a magnet may be evaluated after adhering the magnet. Third, a magnetic field using a permanent magnet may be applied by hand, and an optimum condition may be determined by altering a magnetic field applying time. Fourth, a magnetic field using a permanent magnet may be applied automatically, and an optimum condition may be determined by altering a magnetic field applying time. Fifth, a magnetic field using a permanent magnet may be applied by hand, and an optimum condition may be determined by altering a magnetic field intensity. Sixth, a magnetic field using an electromagnet may be applied by hand, and an optimum condition may be determined by altering a magnetic field applying time. Seventh, a magnetic field using an electromagnet may be applied automatically, and an optimum condition may be determined by altering a magnetic field applying time. Eighth, a magnetic field using an electromagnet may be applied by hand, and an optimum condition may be determined by altering a magnetic field intensity. Ninth, a magnetic field using an electromagnet may be applied automatically, and an optimum condition may be determined by altering a magnetic field intensity.

Several exemplary uses of the blood flow controlling apparatus 100 will now be described.

A first exemplary use involves using an evaluation apparatus or a blood flow control apparatus according to exemplary embodiments of the present invention to determine the effectiveness of a magnet bracelet having a permanent magnet.

In the first exemplary use, a blood flow quantity in a radial artery region is measured for a predetermined amount of time before the magnetic bracelet is put on. Then, the blood flow quantity in the radial artery region is measured again for the same predetermined amount of time after the magnetic bracelet is put on. If the result in the second case is greater than that in the first case, it can be determined that the magnetic bracelet is effective to increase blood flow quantity.

If the magnetic bracelet is determined to be effective, a second exemplary use involves using an evaluation apparatus or a blood flow control apparatus according to exemplary embodiments of the present invention to determine how many hours a day the magnetic bracelet should be worn to be effective for blood circulation.

In the second exemplarily use, an amount of the blood flow in a predetermined region is calculated after wearing the magnetic bracelet for several periods of time. Then, the period of time when the amount of the blood flow reached a maximum is chosen as the optimum amount of time to wear the bracelet.

In a third exemplary use, an evaluation apparatus or a blood flow control apparatus according to exemplary embodiments of the present invention may be used to determine an effectiveness of a magnetic mat with five (5) levels controlled by an electromagnet.

In the third exemplary use, a blood flow amount is measured when the mat is not used. Then, a blood flow amount is measured after turning on and using the mat. If a value of the blood flow amount in the second case is greater than the blood flow amount in the first case, it is determined that the mat is effective to increase an amount of blood flow.

If the magnetic mat is determined to be effective, a fourth exemplary use may involve using an evaluation apparatus or a blood flow control apparatus according to exemplary embodiments of the present invention to determine an optimum power level and optimum time of use for the magnetic mat to be most effective.

In the fourth exemplary use, an amount of blood flow is measured by altering the power while lying down on the magnetic mat so that an applied magnetic field is controlled. For example, the power can be changed from level one to five after a predetermined time, and an increased amount of blood flow can be observed. If the maximum blood flow amount is achieved at level four, then this level is considered the most effective power level.

Then, after use of the magnetic mat begins, the amount of blood flow is calculated as time increases. That is, after the power is set to level four, the blood flow amount is measured for several periods of time to determine the optimum period of time for using the magnetic mat. Thus, it may be determined that it is most effective to use the magnet mat for y hours at an intensity of level four.

Meanwhile, if a user changes, appropriate conditions for the new user can be found and applied after performing the above mentioned operations.

In a fifth exemplary use, the magnetic field applying unit 110 described in the exemplary embodiment of the present inventions can be used as follows. First, before attaching a permanent magnet to the wrist, a blood flow amount in a radial artery region of the wrist is measured for a first time $T_A$. Then, the permanent magnet is attached to the wrist and a blood flow amount is measured for a second time $T_B$, in which the blood flow amount reaches a maximum. As such, a time $T_{MAX}$ when the amount of the blood flow quantity is maximized is found.

Then, a plurality of permanent magnets provided are attached to the wrist for the time $T_{MAX}$ when the amount of blood flow is maximum, and the permanent magnet in which the blood flow amount is maximum is determined. Therefore, the permanent magnet that causes the maximum blood flow amount may be attached to the wrist for time $T_{MAX}$.

When the magnetic field applying unit 110 of the blood flow controlling apparatus 100 uses an electromagnet, a sixth exemplary use may involve measuring a blood flow amount in a radial artery region of the wrist is measured for a first time $T_A$, before attaching the electromagnet to the wrist. Then, after attaching the electromagnet, a blood flow amount in the radial artery region of the wrist is measured for a second time $T_B$, and a time $T_{MAX}$ when the blood flow amount is the maximum is determined.

Therefore, after attaching the electromagnet for the time $T_{MAX}$, the maximum intensity $B_{MAX}$ of the electromagnet when the blood flow amount is maximum is determined by altering the intensity of the electromagnet. As a result, the electromagnet should preferably be used for the time $T_{MAX}$ at an intensity of $B_{MAX}$ Gauss.

According to above-mentioned exemplary embodiments of the present invention, by measuring blood flow near the wrist of a living body and providing feedback of the results to a user, the blood flow can be improved more efficiently using a magnetic field. Additionally, the blood flow can be measured with ease and controlled without harming the user.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A blood flow controlling apparatus using a magnetic field for controlling blood flow within a living body, the blood flow controlling apparatus comprising:
    a magnetic field applying unit for supplying the magnetic field and applying the magnetic field to the living body;
    a blood flow measuring unit for measuring a blood flow signal including information about blood flow; and
    a blood flow controlling unit for controlling the blood flow according to the measured blood flow signal,
    wherein the blood flow controlling unit comprises: a magnetic field intensity calculator for calculating an intensity of the magnetic field applied to the living body; and
    a magnetic field applying time calculator for calculating a time the magnetic field is applied to the living body.

2. The blood flow controlling apparatus as claimed in claim 1, wherein the blood flow controlling unit is operable to provide biofeedback of the measured blood flow signal.

3. The blood flow controlling apparatus as claimed in claim 1, wherein the blood flow controlling unit comprises:
    a blood flow quantity and blood flow difference calculator for calculating a blood flow quantity and a blood flow difference;
    the magnetic field intensity calculator;
    the magnetic field applying time calculator; and
    a controller for controlling the magnetic field intensity calculator and the magnetic field applying time calculator using the blood flow quantity and the blood flow difference calculated by the blood flow quantity and blood flow difference calculator.

4. The blood flow controlling apparatus as claimed in claim 3, further comprising a mode selecting unit for selecting from a plurality of modes.

5. The blood flow controlling apparatus as claimed in claim 4, wherein the mode selecting unit is operable to select one mode from the group consisting of a blood flow improvement evaluation mode, a blood flow quantity monitoring mode, an optimum condition determination mode, and a blood flow improving mode, and wherein the selected mode is input to the controller of the blood flow controlling unit.

6. The blood flow controlling apparatus as claimed in claim 5, wherein the optimum condition determination mode comprises an optimum magnetic field applying time determining mode, an optimum magnetic field intensity determining mode, and an optimum magnetic field intensity and applying time determining mode.

7. The blood flow controlling apparatus as claimed in claim 1, further comprising an outputting unit.

8. The blood flow controlling apparatus as claimed in claim 7, wherein the outputting unit displays data selected from the group consisting of blood flow quantity, blood flow difference, and optimum magnetic field intensity and applied time, obtained by the blood flow controlling unit, and wherein the outputting unit displays information so that a user may control a blood flow controlling apparatus software including one or more items selected from the group consisting of a start menu, a mode selection menu, and a user history menu.

9. The blood flow controlling apparatus as claimed in claim 7, wherein the outputting unit is an output device that outputs data obtained by the blood flow controlling unit in a manner selected from print, an audio signal, a two-dimensional visual image, and moving images.

10. The blood flow controlling apparatus as claimed in claim 7, wherein the outputting unit is an output device that displays data obtained from the blood flow controlling unit while measuring the blood flow in real-time.

11. The blood flow controlling apparatus as claimed in claim 7, wherein the outputting unit is an output device for analyzing data obtained from the blood flow controlling unit and for additionally outputting medical information or diagnosis.

12. The blood flow controlling apparatus as claimed in claim 1, wherein the magnetic field applying unit comprises a monopole stimulus.

13. The blood flow controlling apparatus as claimed in claim 1, wherein the magnetic field applying unit comprises a first magnet having a north pole and a second magnet having a south pole, the north pole of the first magnet being adhered to the south pole of the second magnet.

14. The blood flow controlling apparatus as claimed in claim 1, wherein the blood flow measuring unit is operable to use an electrical impedance method including impedance plethysmography (IPG).

15. The blood flow controlling apparatus as claimed in claim 1, wherein the blood flow measuring unit is operable to measure a radial artery region of a wrist.

16. A blood flow evaluating apparatus for examining an effect on blood flow of an apparatus that applies a magnetic field to a predetermined region of a living body, the blood flow evaluating apparatus comprising:
    a blood flow measuring unit for measuring a blood flow signal including information about blood flow;
    a blood flow quantity and blood flow difference calculator for calculating a blood flow quantity and a blood flow difference using the blood flow signal measured according to an applied magnetic field;
    a magnetic field applying time calculator for calculating a time the magnetic field is applied to the living body, and a magnetic field intensity calculator for calculating an intensity of the magnetic field applied to the living body; and
    wherein an improvement in blood flow is evaluated using the calculated blood flow quantity and the blood flow difference.

17. A blood flow controlling apparatus using a magnetic field, the blood flow controlling apparatus comprising:
    a magnetic field applying unit for applying the magnetic field to a predetermined region of a living body;
    a blood flow measuring unit for measuring a blood flow signal including information about blood flow;
    a mode selecting unit for selecting from among a plurality of modes by a user;
    a blood flow quantity and blood flow difference calculator for calculating a blood flow quantity and a blood flow difference using the blood flow signal;
    a controlling unit for generating a control signal according to a mode selected by the mode selecting unit; and
    a magnetic field controlling unit for controlling the magnetic field using the control signal and the blood flow quantity and difference, and applying the magnetic field to the predetermined region, wherein the magnetic field controlling unit includes a magnetic field applying time calculator for calculating a time the magnetic field is applied to the living body, and a magnetic field intensity calculator for calculating an intensity of the magnetic field applied to the living body.

18. The blood flow controlling apparatus as claimed in claim 17, wherein the mode selecting unit may select one mode from the group consisting of mode 0 through mode 4, where mode 0 is for evaluating blood flow improvement, mode 1 is for monitoring the blood flow quantity, mode 2 is determining an optimum magnetic field applying time for improving the blood flow using the magnetic field applying time calculator, mode 3 is for determining an optimum magnetic field intensity for improving the blood flow using the magnetic field intensity calculator, and mode 4 is for controlling an optimum blood flow using the magnetic field applying time calculator and the magnetic field intensity calculator.

* * * * *